United States Patent [19]

Kaplan et al.

[11] 4,214,596

[45] Jul. 29, 1980

[54] PERMANENT WAVE SYSTEM USING AMMONIUM BISULFITE PREWRAP

[75] Inventors: Julius F. Kaplan, Highland Park; Norman L. Edelberg, Vernon Hills; Chester A. Davis, Berwyn, all of Ill.

[73] Assignee: Helene Curtis Industries, Inc., Chicago, Ill.

[21] Appl. No.: 929,326

[22] Filed: Jul. 31, 1978

[51] Int. Cl.$^2$ .............................................. A45D 7/00
[52] U.S. Cl. .......................................... 132/7; 424/72
[58] Field of Search ............................. 132/7; 8/10.2; 424/71-72

[56] References Cited

U.S. PATENT DOCUMENTS

| | | | |
|---|---|---|---|
| 2,351,718 | 6/1944 | Speakman | 132/7 |
| 2,615,828 | 10/1952 | Haefele | 132/7 X |
| 2,836,185 | 5/1958 | Hervey | 132/7 |
| 3,472,604 | 10/1969 | Dasher et al. | 8/10.2 |
| 3,533,417 | 10/1970 | Bartoszewicz | 132/7 |

OTHER PUBLICATIONS

M. S. Balsam & Edward Sagarin–Cosmetics, Mar. 1972, pp. 208–209.

*Primary Examiner*—G. E. McNeill
*Attorney, Agent, or Firm*—Dressler, Goldsmith, Shore, Sutker & Milnamow, Ltd.

[57] ABSTRACT

This invention relates to an improvement in the method of treating hair in which water wet hair is wrapped around rollers, a mercaptan-containing solution is applied to the hair on the rollers, and the mercaptan-wetted hair is thereafter neutralized with an oxidizing agent. This improvement comprises wetting the hair prior to wrapping it with an aqueous solution of a prewrap agent selected from the group consisting of alkali metal and ammonium sulfites and alkali metal and ammonium bisulfites. These prewrap agents are present at about 0.1 to about 1.0 Molar, at a pH of about 6.5 to about 7.5 and cleave no more than about 5 percent of the hair disulfide bonds before the mercaptan-containing solution is applied.

9 Claims, No Drawings

PERMANENT WAVE SYSTEM USING AMMONIUM BISULFITE PREWRAP

BACKGROUND OF THE INVENTION

This invention relates to an improvement in hair treatments in which moistened hair is placed on rollers or rods (hereinafter "rollers"), hair protein disulfide bonds which cross-link the hair are broken by use of thiol-containing reagents, and then the disulfide bonds are reformed by use of an oxidizing neutralizer which causes the hair to acquire a new curl. The improvement of our invention involves the use of a bisulfite or sulfite containing aqueous solution which is applied to the hair prior to wrapping the hair on the rollers.

Thiol-containing reagents for hair treatments are those materials which contain a free —SH group or mercaptan. Salts of thioglycolate acids and thioglycolic acid esters are the reagents which are normally used in such hair treatments. Other thiol-containing reagents such as thiolactic acid, $\beta$-mercaptopropionic acid, $\beta$-mercaptobutyric acid, and the like are known in the art to be effective.

While hair treatments with thiol containing reagents used in conjunction with hair rollers are most frequently used for waving hair, i.e., putting in curl, these reagents may be used with rollers for straightening hair, i.e., taking some curl from curly hair. When a tight curl is wanted as in waving, curlers of a narrow diameter, such as about 1 cm or less, are used. For straightening, curlers of a wide diameter, such as about 5 cm, may be used. The improvement of this invention relates to both waving and straightening hair, although its primary uses will probably be in the field of hair waving. For convenience, the word "waving" is used hereinbelow to mean hair treatments which include both waving and straightening. Thus, those methods for imparting a tighter curl when a narrow diameter roller is used will also impart a looser curl when a wide diameter roller is used.

The process of waving hair is old in the art and will not be explained in detail herein. Generally, in such processes, dampened hair is wound about a roller or curler and clamped in place. A solution containing the mercaptan reagent (waving lotion) is then applied to the hair upon the rollers to cleave the disulfide bonds within the hair. After waiting a suitable period of time, the waving lotion is rinsed from the hair. The hair is then neutralized with an oxidizing reagent which reforms disulfide bonds within the hair that had been broken by the thiol-containing reagent. It is believed that the reformation of the disulfide bonds within the hair is what causes the new wave or curl to be imparted to the hair. The curls so imparted will not wash out with water and consequently a curl or wave so formed is called a permanent wave. When this process is carried out at room temperature, without the use of external heating devices, it is called "cold waving."

Modern, commercial, cold, permanent waving preparations frequently include an instruction to wet the hair with the waving solution or lotion prior to wrapping the hair upon the rollers. It has been found that such a prewrap treatment helps impart a tighter curl to the hair than if water, alone, is used to wet the hair prior to wrapping. A problem with such a prewrapping procedure however, is that although manufacturers suggest that gloves be worn during the wrapping procedure, the person, such as the hair dresser, who would do the wrapping usually finds that the use of gloves makes such wrapping quite difficult and cumbersome to achieve. As a consequence of this difficulty, many such users do not wear gloves during the wrapping process. Frequent and/or prolonged contact of the user's hands with the waving solution and its thiol containing reagent often causes skin irritation and in some cases causes allergic reactions. This is true even where the safest thiol-containing reagents, such as thioglycolic acid derivatives, are used. Thus, the hair dresser is frequently faced with the problems of getting a loose curl when a tight curl is desired because a prewrap solution of water was used rather than waving lotion, or of getting irritated skin from handling the waving lotion without gloves.

While the general cold waving process is old in the art, there has been an evolution in the pH and constituents of the waving lotion. As originally introduced, the waving lotion pH was approximately 9.2 or higher. More recently cold waving has been practiced at a pH as low as about 7.6. Still more recently so-called "acid" waving has been introduced. The pH of an acid waving solution is approximately 6.9 or lower. While the principal waving constituent in the older waving lotions was a salt of thioglycolic acid, such as ammonium thioglycolate, the acid waving lotions usually contain glyceryl monothioglycolate as the principal active ingredient.

While there are several advantages to using an acid waving system, there are also disadvantages. One important disadvantage to these systems is that they are more injurious to skin than were the more basic ammonium thioglycolate based, waving lotions. Consequently, most manufacturers do not suggest using the acid waving lotion as a prewrap solution because it is known that some users don't wear gloves during the wrapping step. With no prewrapping solution or, in effect, a water prewrapping solution, curl tightness often suffers.

One benefit of our invention is to lessen the contact of the mercaptan-containing reagent with the user's hands by providing an alternative prewrap solution which does not contain a mercaptan reagent.

Another benefit of our invention is to provide a prewrap solution which will allow the formation of a tighter curl than is possible by using only water as the prewrap solution.

BRIEF SUMMARY OF THE INVENTION

This invention relates to an improvement in the method of treating hair in which water wet hair is wrapped around rollers, a mercaptan-containing solution is applied to the hair on the rollers, and the mercaptan-wetted hair is thereafter neutralized with an oxidizing agent. This improvement comprises wetting the hair prior to wrapping it with an aqueous solution of a prewrap agent selected from the group consisting of alkali metal and ammonium sulfites and alkali metal and ammonium bisulfites. These prewrap agents are present at about 0.1 to about 1.0 Molar, at a pH of about 6.5 to about 7.5 and cleave no more than about 5 percent of the hair disulfide bonds before the mercaptan-containing solution is applied.

DETAILED DESCRIPTION OF THE INVENTION

We have found that aqueous solutions containing prewrap agents such as sulfite and bisulfite salts are particularly mild to the user's hands when used in place of waving lotion in a prewrap solution, and that such solutions provide waved hair having a tighter curl than if water alone is used as a prewrap solution. The sulfite and bisulfite salts which are preferred as prewrap agents in our invention are the alkali metal and ammonium salts. These include sodium sulfite heptahydrate, potassium sulfite dihydrate, ammonium sulfite monohydrate and the like as well as sodium, potassium and ammonium bisulfites and the like. Ammonium bisulfite is particularly preferred.

The concentrations of these preferred prewrap agents in the aqueous prewrap solution can range from about 0.1 Molar to about 1.0 Molar. The preferred range is about 0.2 Molar to about 0.3 Molar.

At a given pH, the amount of disulfide bond cleavage is dependent at least upon the concentration of sulfite or bisulfite prewrap agents, the duration of contact of these prewrap agents with the hair and the temperature at which these reagents are used to treat the hair. High concentrations, long contact times and elevated temperatures are factors which promote increased disulfide bond cleavage. Therefore, these factors may be altered or played against each other to produce a desired amount of disulfide bond rupture. In practicing the method of our invention, the preferred concentration of sulfite or bisulfite, placed on the hair without external heating, allows the user a leisurely pace for applying the waving lotion so that the lotion is applied before too many disulfide bonds are broken by the prewrap agents.

Although sulfite and bisulfite salts are known in the art for use in waving hair, the methods of such use as taught in the art and as practiced herein are different. In waving, at least about 15 percent, and preferably about 20 to about 30 percent of the disulfide bonds are broken by the waving lotion, using virgin, European hair as the standard. As practiced in our prewrap method, no more than about 5 percent of the disulfide bonds in virgin, European hair are broken by the sulfite or bisulfite salts of the prewrap solution. While these salts may be used to practice our invention at a concentration of about 1 Molar, as is frequently practiced in the waving art, the user must work quickly at such concentrations to avoid breaking too many disulfide bonds to thereby avoid forming too many Bunte salt groups [Protein—$SSO_3$—] which remain in the hair after waving. Problems associated with excessive residual Bunte salt groups are discussed hereinbelow. By using the preferred concentration of about 0.2 Molar to about 0.3 Molar, the user need not rush as such concentrations will not cleave the minimal 15 percent disulfide bonds needed for waving within normal working times.

Another difference between the bisulfite waving art and that of our invention is that the sulfhydryl groups (Protein—SH) and the Bunte salt groups [Protein—S-$SO_3$—] formed in either method by the action of bisulfite or sulfite ions with the disulfide bonds of the hair protein are reformed into disulfide bonds in the conventional waving processes with the aid of a fixing step carried out at a pH of about 8 to about 10, while in our invention, no such fixing step is used and the hair protein disulfide bonds are reformed by the oxidizing neutralizer which is used in conjunction with the mercaptan-containing waving lotion. If sufficient amounts of Bunte salt groups are present to allow waving to occur, i.e., greater than about 15 percent, oxidative neutralization as practiced herein leaves the hair harsh to the touch, brittle when dry and spongy when wet. However, as practiced by our method, fewer than about 5 percent Bunte salt groups are formed prior to application of the waving lotions, and, there is little tendency toward harsh feeling, brittle hair after oxidative neutralization.

U.S. Pat. No. 3,644,084 to Hsiung and Wolfram discloses a method for reforming hair disulfide bonds broken by sulfitolysis. In their method, the hair disulfide bonds are cleaved by use of a sulfite type reagent and the bonds are reformed by a sulfur-containing reagent (including a mercaptan) present at about 0.02 to 0.3 Molar. In our method, only a small amount of the disulfide bonds (less than about 5 percent) are cleaved by sulfite reagents, while the great majority of bonds are broken by the mercaptan-containing reagent present, as in commercial waving lotion, at about 0.5 to about 2.5 Molar. The Hsiung and Wolfram method includes a step, not found in our method, in which sulfite reagent is rinsed from the hair prior to application of the sulfur-containing reagent.

Essentially, the Hsiung and Wolfram method starts with a strong sulfite treatment (to cleave more than 15 percent of the disulfide bonds) and follows it with a weak mercaptan treatment (to reform the already cleaved disulfide bonds). In contrast, the instant invention starts with a weak sulfite treatment (to cleave fewer than about 5 percent of the disulfide bonds) and follows it with a strong mercaptan treatment (to cleave the remaining bonds necessary to provide a good wave).

The Hsiung and Wolfram patent also discloses an analytical method for determining the amounts of Bunte salt groups and Protein—SH groups in the hair as well as the residual amounts of these groups after reformation of the disulfide bonds. The first step of this analytical method is hereby incorporated by reference for determining the amount of disulfide bond cleavage caused by the prewrap solution of our invention. The ratio of disulfide bond cleavage to total disulfide present, as found by the MNP method, times 100 percent yields the percent disulfide bond rupture as discussed herein.

Additionally, in bisulfite waving, the usual practice is to treat the hair, wound on rods or rollers, with waving lotion, cover the hair with a plastic turban for 10 to 20 minutes, rinse, treat the hair with fixing lotion, followed by another rinse and then the neutralization step. In our method, the moistened hair is simply treated with our prewrap formulation to achieve limited disulfide cleavage, wound on rollers and then treated with a mercaptan containing waving lotion.

The preferred pH of the prewrap solutions of our invention is about 6.5 to about 7.5. More preferred is a pH of about 6.9 to about 7.0. This preferred pH range is also the pH range at which many commercial waving lotions, including the acid waving lotions are supplied and thus, there is little if any problem of pH incompatibility between the prewrap solution and the waving lotion. The prewrap solutions of our invention also have a minimal buffering capacity so that if a buffered waving lotion of a higher pH is used, the pH of the prewrap solution does not greatly affect that of the waving lotion. Because of the bisulfite-sulfite equilibrium, the bisulfite ion predominates in solution at pH values less than about 7.2.

To use the prewrap solutions of our invention, the hair to be waved is usually first dampened. This usual dampening is often the result of a prior shampoo treatment although such a shampooing is not necessary to practice this invention. After such a dampening or shampoo treatment, the hair is preferably towelled dry so that it is not dripping wet. An aqueous prewrap solution of this invention is then applied to the hair. The prewrap solution treated hair is then wrapped upon rollers of the desired diameter, and the hair treated with the mercaptan-containing waving lotion and oxidizing neutralizer as is the usual practice in the art. Upon drying, the curls obtained are tighter than those obtained when water alone is used as a prewrap liquid.

The prewrap solutions used in the practice of this invention are usually formulated to contain emulsifiers, conditioners, swelling agents, preservatives, perfumes, coloring agents and the like. These added materials enhance the effect and appearance of the product and treated hair, but are not necessary for the practice of our invention.

The present invention is illustrated by, but not limited to the following examples.

EXAMPLE 1: Ammonium Bisulfite Prewrap Lotion

A specific ammonium bisulfite containing prewrap lotion was prepared as follows:

FORMULA

| Components | | Percent by Weight |
|---|---|---|
| (1) | Deionized water | 90.00 |
| (2) | Ammonium bisulfite (60%) | 5.40 |
| (3) | Ammonium sulfate | 0.50 |
| (4) | Ascorbic acid | 0.10 |
| (5) | Ammonium hydroxide to pH 6.5–6.8 approx. | 1.25 |
| (6) | Ceraphyl 65[1] | 0.20 |
| (7) | Tween 20[2] | 0.40 |
| (8) | Fragrance | 0.05 |
| (9) | Coloring solutions | 0.025 |
| (10) | NH$_4$OH to pH 6.9–7.0 | — |
| (11) | Deionized water | balance |
| | | 100.00 |

[1]An amide formed from mink oil fatty acid and 1-amino-propyl-3,3-dimethyl-3-β-hydroxyethylammonium chloride.
[2]Polyoxyethylene sorbitan monolaurate.

Components 3 and 4 were dissolved in component 1. Component 5 was added followed by component 2. Components 6, 7 and 8 were premixed and added to the above mixture with agitation. The final components, 10 and 11 were added and the entire mixture agitated to ensure homogeneity.

EXAMPLE 2: Acid Waving Formulation

Portion A—Glyceryl Monothioglycolate

Glyceryl monothioglycolate is an item of commerce which typically contains about 80 percent by weight glyceryl monothioglycolate, about 1 percent to about 6 percent by weight free thioglycolic acid, with the remainder of the material being free glycerol. Portion A is packaged separately from Portions B and C.

Portion B—Buffered Base

FORMULA

| Components | Weight Percent |
|---|---|
| (1) Deionized water | 96.05 |
| (2) Borax | 1.00 |
| (3) Dantoin MDMH[1] | 0.10 |
| (4) Igepal CO 730[2] | 0.75 |
| (5) Fragrance | 0.10 |
| (6) Ammonium hydroxide 28% | app. 2.00 |
| | 100.00 |

-continued
FORMULA

| Components | Weight Percent |
|---|---|
| solution pH is 9.9–10.1 | |

[1]Monomethylol dimethylhydantoin.
[2]Nonylphenol condensed with ethylene oxide to about 73% of the phenol's weight.

Components 1–5 may all be added together and mixed, component 6 is added last and then mixed in thoroughly.

About 29.4 gm of Portion A are mixed with about 78.0 gm of Portion B to yield a buffered, acid waving formulation whose pH is about 6.9.

Portion C—Oxidizing Neutralizer

A typical oxidizing neutralizer solution comprises:

FORMULA

| Components | Weight Percent |
|---|---|
| 1) Deionized water | 92.252 |
| 2) Fatty acid quaternary ammonium complex[1] | 1.500 |
| 3) Hydrogen peroxide (35% aqueous) | 6.230 |
| 4) Silicone antifoam agent | 0.010 |
| 5) Phosphoric acid to pH 3.5 | app. 0.008 |
| | 100.000 |

[1]The fatty acid quaternary ammonium complex is a conditioning agent which serves to improve the combability of the finished waves.

Components 1–4 may all be added together and mixed with component 5 added last and then mixed in thoroughly.

EXAMPLE 3: Waving Hair Using A Prewrap Formulation

Models' heads were shampooed and rinsed in a usual fashion and then towelled so that while they were wet, they were not dripping wet. One side of their heads was then wrapped (while the hair was wet) on standard waving rollers. The other side of the models' heads was treated with the prewrap formulation of Example 1 by pouring the formulation onto the hair, working it into the hair and then wrapping sections of the treated hair onto rollers identical to those used on the water-only treated sides. Portions A and B of Example 2 were mixed as discussed in Example 2 and applied to the rolled hair on both sides of the heads as soon as the wrapping operation was completed (within about 15–45 minutes, depending on the speed of the operator and the hair of the model). After a suitable time, up to about 30 minutes, depending upon the models' hair type and desired curl tightness, the prewrap solution and waving lotion were rinsed from the hair. Portion C of Example 2 was added to the rolled hair on both sides of the heads. The neutralizer was then rinsed from the hair, and the hair dried. Evaluations for curl tightness for each half-head showed that those half-heads treated with the prewrap formulations of this invention had tighter curls than those treated with water alone.

While the invention has been described with respect to its preferred embodiments, it will be understood by those skilled in the art that modifications and variations may be made without departing from the invention as defined in the appended claims.

We claim:

1. In the method of treating of hair in which water-wet hair is wrapped around rollers, an aqueous mercaptan-containing solution having a pH not higher than about 6.9 is applied to the hair on the rollers to cleave disulfide bonds in said hair, and the mercaptan-wetted hair is thereafter neutralized with an oxidizing agent to reform disulfide bonds in said hair, the improvement which comprises wetting said hair, prior to said wrapping thereof, with an aqueous solution of a prewrap agent of the group consisting of alkali metal and ammonium sulfites and alkali metal and ammonium bisulfites, said prewrap agent being present in said aqueous solution at a concentration of about 0.1 Molar to about 1.0 Molar, said prewrap agent being at a strength and applied for a period such that no more than about 5% of the disulfide bonds in said hair are cleaved by said prewrap agent prior to said application of said mercaptan-containing solution and being maintained on said hair during the application of said mercaptan-containing solution.

2. The method of claim 1 wherein the pH of said aqueous prewrap agent containing solution is about 6.5 to about 7.5.

3. The method of claim 1 wherein said prewrap agent is present in said aqueous solution at a concentration of about 0.2 Molar to about 0.3 Molar.

4. In the method of permanent waving of hair in which hair wet with water is wrapped around rollers, an aqueous thioglycolate solution having a pH not higher than about 6.9 is applied to the hair on the rollers to cleave disulfide bonds in said hair, and the thioglycolate-wetted hair is thereafter neutralized with an oxidizing agent to reform disulfide bonds in said hair, the improvement which comprises wetting said hair prior to said wrapping thereof with an aqueous solution at a pH of about 6.5 to about 7.5 of a prewrap agent of the group consisting of alkali metal and ammonium sulfites and alkali metal and ammonium bisulfites, said prewrap agent being present in said aqueous solution at a concentration of about 0.1 Molar to about 1.0 Molar, said prewrap agent being at a strength and applied for a period such that no more than about 5% of the disulfide bonds in said hair are cleaved by said prewrap agent prior to said application of said mercaptan-containing solution and being maintained on said hair during the application of said thioglycolate solution.

5. The method of claim 4 wherein the pH of said aqueous prewrap agent containing solution is about 6.9 to 7.0.

6. The method of claim 4 wherein said prewrap agent is present in said solution at about 0.2 Molar to about 0.3 Molar.

7. The method of claim 4 wherein said prewrap agent is ammonium bisulfite.

8. The method of claim 4 wherein said thioglycolate is glyceryl thioglycolate.

9. In the method of permanent waving of hair in which hair wet with water is wrapped around rollers, an aqueous glyceryl thioglycolate solution is applied to the hair on the rollers to cleave disulfide bonds in said hair, and the glyceryl thioglycolate-wetted hair is thereafter neutralized with an oxidizing agent to reform disulfide bonds in said hair, the improvement which comprises wetting said hair, prior to said wrapping thereof, with an aqueous solution of a pH of about 6.9 to about 7.0 of ammonium bisulfite prewrap agent present at about 0.2 Molar to about 0.3 Molar, said prewrap agent being applied for a period such that no more than about 5% of the disulfide bonds in said hair are cleaved by said prewrap agent prior to said application of said mercaptan-containing solution and being maintained on said hair during the application of said glyceryl thioglycolate solution.

* * * * *